United States Patent [19]

Zampini

[11] Patent Number: Plant 7,062

[45] Date of Patent: Dec. 5, 1989

[54] FLOWERING CRAB APPLE TREE NAMED SUTYZAM

[76] Inventor: James W. Zampini, 5052 S. Ridge Rd., Box 122, Perry, Ohio 44081

[21] Appl. No.: 259,070

[22] Filed: Oct. 18, 1988

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Watts, Hoffmann, Fisher & Heinke Co.

[57] ABSTRACT

A new and distinct variety of flowery Malus crab apple tree, substantially as herein shown and described, characterized particularly by a combination of a profusion of annual bloom and extremely long-persisting, highly-ornamental fruit.

1 Drawing Sheet

DESCRIPTION

The present invention relates to a new and distinct variety of Crab Apple, Malus Sutyzam. This variety was discovered in 1965 in Zone 5 as a hybrid seedling variant growing with several others under its seed parent *Malus zumi* 'Calocarpa' in the garden of Professor Milton Baron at 1313 Buckingham Road, Haslett, Mich. 40840.

Figure 1:
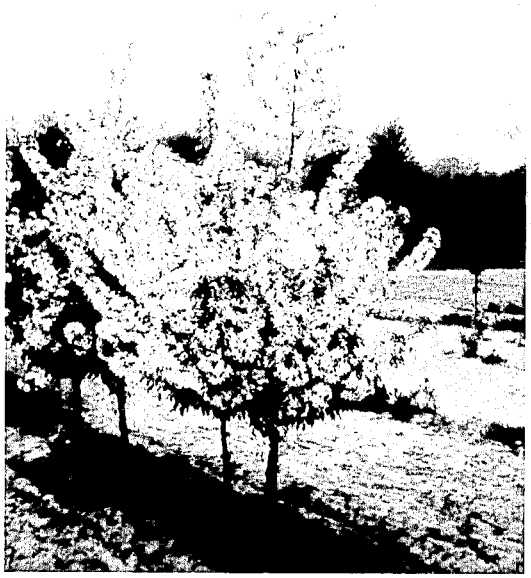
FIG. 1 shows my new flowering crab apple tree with flower in full bloom.
Figure 2:
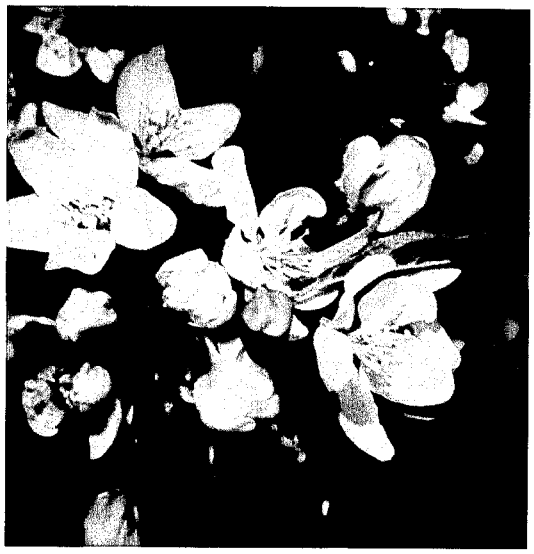
FIG. 2 shows a branchlet of such tree illustrating the flower thereof.
Figure 3:
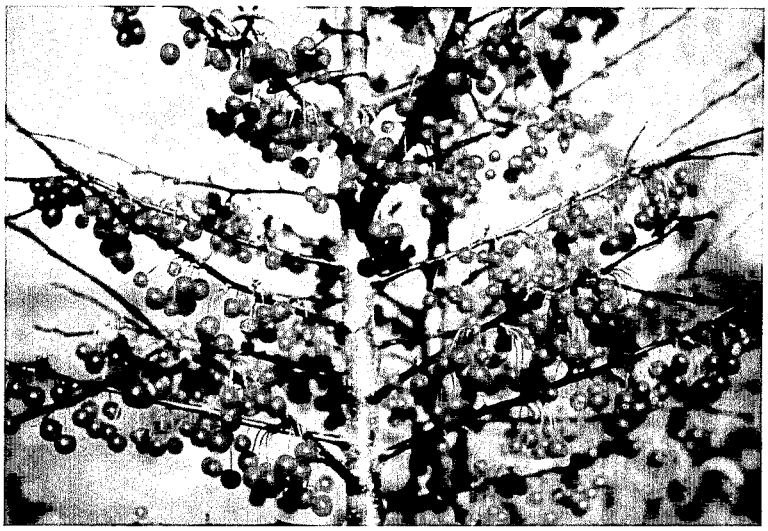
FIG. 3 shows a portion of such tree illustrating the fruit thereof.

This selection has a unique and novel combination of a profusion of annual bloom and extremely long-persisting, highly ornamental fruit. This combination readily distinguishes it from the seed parent and other varieties of the genus.

The flower of this selection are pale pink in bud and snowy white when fully expanded. The fruit retains its bright luster throughout its long period of effectiveness, which ranges from mid-October until (or sometimes even beyond) the following year's blooming period. The fruit color, initially deep red with a somewhat paler check, gradually changes to a rich maroon and eventually to a lustrous cordovan brown.

Deep green foliage and vigorous growth rate well above average for the genus attracted initial attention to this selection. In normal seasons and sites a growth increment of two or more feet per year has been observed. The multiple-stem crown develops wide crotches and a broadly upright form. It is presently 18 feet tall, 18 feet wide and has a caliper of seven inches at grade. If grown on its own roots it is expected to reach a height approximating 30 feet at maturity.

If desired, this mature size can be reduced by budding or grafting on dwarfing rootstocks as has been demonstrated by successful unions with *Malus sargenti;* if the original seedling vigor is desired, propagation by softwood cuttings has repeatedly been demonstrated to be 80% or more successful. A further advantage horticulturally is the exceptional ease of transplanting in comparison even to other crab apples.

The principal distinguishing feature of this new variety is the combination of its profuse, annually-produced and highly-ornamental bloom together with its persistent, frost-tolerant and likewise showy fruit.

Particularly distinctive is the extremely long persistence of the continuously lustrous fruit, together with the predictable color changes it undergoes through autumn, winter and spring. At maturity, in mid to late October, the rich red hue matches Ridgway Oxblood Red on Plate I, on the check side Scarlet Red (Ridgway, Plate I). Through the winter season, the color darkens to a deep maroon approximating Ridgway Maroon (Plate I), and finally by early spring — provided migrant seed-eating birds permit — it reaches Ridgway Claret red (Plate I).

The vegetative and reproductive parts of this variety are in most other respect typical of the genus. The alternate, simple, ovate to broadly lanceolate leaves are dark green above and paler beneath. The margins are sharply serrate, remotely so near the base. Initially moderately white-villous, the blades at maturity are glabrous except along the veins below. Leaves of vegetative shoots reach 5" in length, of which about 1" represents petiole. Leaves of fruiting shoots are variably smaller in all dimensions. Immature twigs are purple-brown and initially moderately white to gray villous. Year-old twigs are light brown and essentially glabrous. Winter buds are cordovan-brown and glabrous except for the densely white villous margins of the bud scales.

The flowers are typical of the genus. Markedly fragrant, they are borne in clusters of 3–5 on slender pedicels $1\frac{1}{4}$" long arising from fruiting spurs about $\frac{3}{8}$" long. Averaging about $1\frac{1}{8}$" across, the fully expanded, snow-white corolla consists of 5 broadly spatulate petals narrowing abruptly to slender claws about $\frac{1}{4}$" long. The slender, acute calyx lobes are reflexed.

The decidedly frost-tolerant fruit is a small, slightly elongated pome containing 3 to 5 single-seeded locules. The fruit averages a little more than $\frac{1}{2}$" long and ranges from $\frac{3}{8}$ to $\frac{1}{2}$" in diameter. Covered with a faint waxy bloom, it is also sparsely flecked with minute silvery glands. The calyx is deciduous, its circular scar surrounding the clearly marked scars of the petals, stamens and styles.

I claim:

1. A new and distinct variety of flowerly Malus crab apple tree, substantially as herein shown and described, characterized particularly by a combination of a profusion of annual bloom and extremely long-persisting, highly-ornamental fruit.

* * * * *